United States Patent [19]
Reher et al.

[11] Patent Number: 5,618,175
[45] Date of Patent: Apr. 8, 1997

[54] PLASTIC ORTHODONTIC BRACKET HAVING ROTATION WINGS

[75] Inventors: James F. Reher, Pomona; Craig A. Andreiko, Alta Loma; David L. Ludwig, San Juan Capistrano, all of Calif.

[73] Assignee: Ormco Corporation, Glendora, Calif.

[21] Appl. No.: 517,432

[22] Filed: Aug. 21, 1995

Related U.S. Application Data

[63] Continuation of Ser. No. 488,059, Jun. 7, 1995, which is a continuation-in-part of Ser. No. 391,663, Feb. 21, 1995.

[51] Int. Cl.$^6$ .................................................. A61C 7/28
[52] U.S. Cl. ........................................ 433/8; 433/16
[58] Field of Search .............................. 433/8, 9, 10, 16, 433/17, 20, 22

[56] References Cited

U.S. PATENT DOCUMENTS

| | | |
|---|---|---|
| 3,930,311 | 1/1976 | Andrews . |
| 4,299,569 | 11/1981 | Frantz . |
| 4,661,059 | 4/1987 | Kanno . |
| 5,044,945 | 9/1991 | Peterson ................................ 433/8 |
| 5,095,602 | 3/1992 | Reher et al. ......................... 433/8 |
| 5,161,969 | 11/1992 | Pospisil et al. ..................... 433/8 |
| 5,174,254 | 12/1992 | Meritt ................................... 433/8 |
| 5,254,002 | 10/1993 | Reher et al. . |
| 5,267,854 | 12/1993 | Schmitt . |
| 5,299,934 | 4/1994 | Suyama .............................. 433/8 |
| 5,380,196 | 1/1995 | Kelly et al. ......................... 433/10 |

OTHER PUBLICATIONS

Metal Bracket Style dated Mar., 1986.
Brochure, "The Mini Wick™ System", Ormco Corporation, ©1985 by Ormco/Division of Sybron Corporation.
Ormco Catalog, Table of Contents, pp. 5, 9, 10 and 15, ©1990 by Ormco Corporation.

*Primary Examiner*—Paul J. Hirsch
*Attorney, Agent, or Firm*—Wood, Herron & Evans, PLL

[57] ABSTRACT

This invention is directed to a plastic orthodontic bracket reinforced with a metal insert having rotation wings. The bracket includes a protrusion extending into the archwire slot and having an upper end elevated above the bottom wall of the archwire slot. The upper end of the protrusion is adapted to contact the underside of an orthodontic archwire located in the archwire slot and to support at least a portion of the archwire above the bottom wall of the archwire slot.

23 Claims, 2 Drawing Sheets

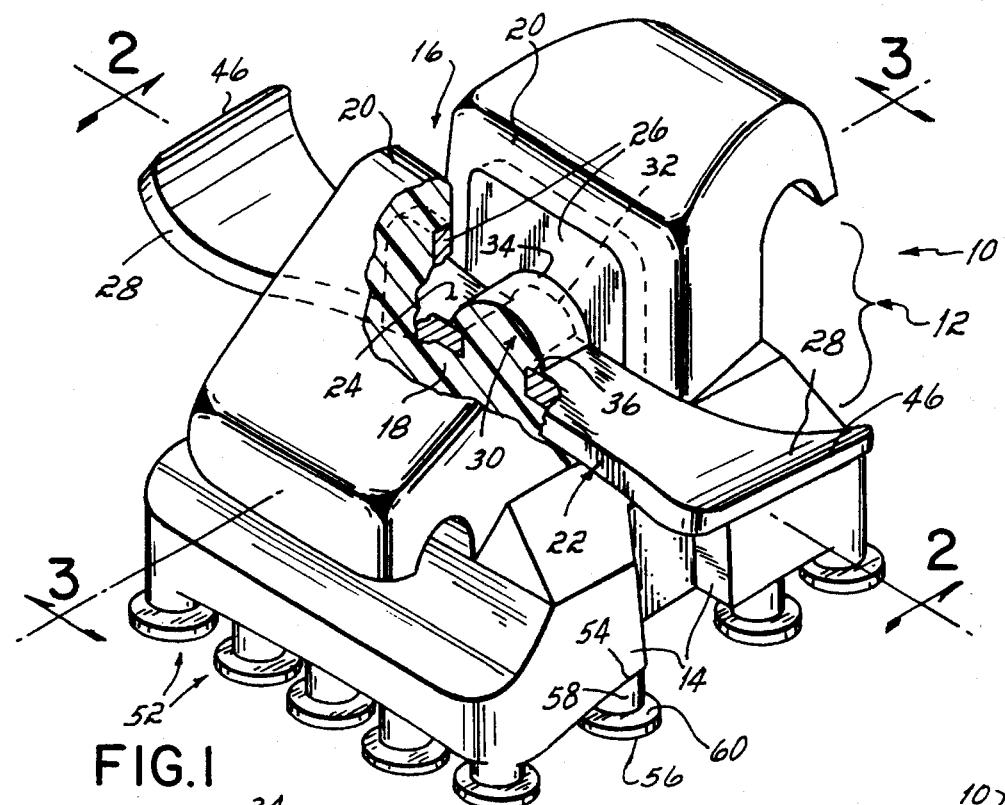
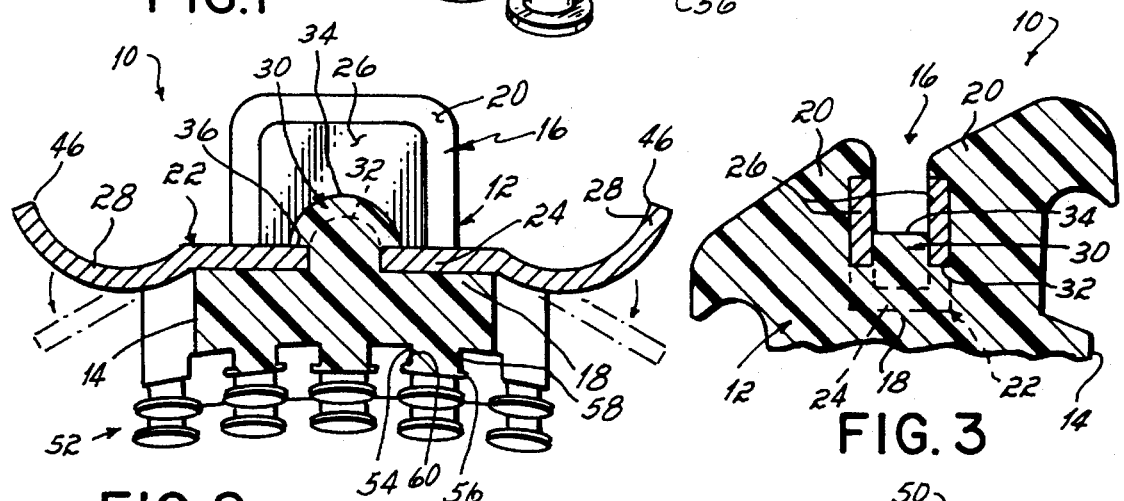
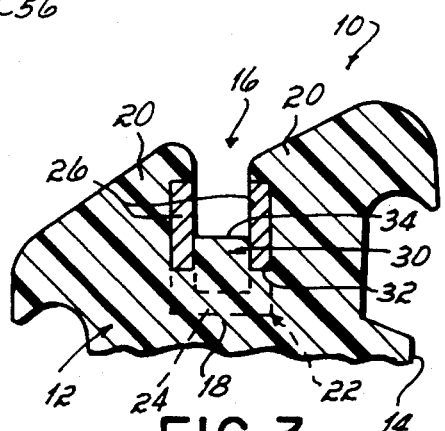
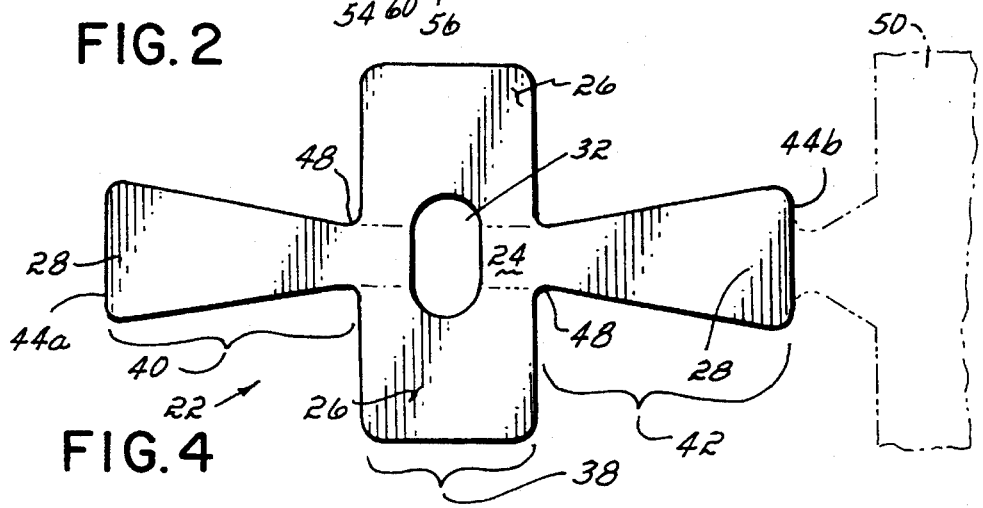

PLASTIC ORTHODONTIC BRACKET HAVING ROTATION WINGS

This application is a continuation of application Ser. No. 08/488,059 entitled "PLASTIC ORTHODONTIC BRACKET HAVING ROTATION WINGS," filed Jun. 7, 1995, which is a continuation-in-part of application Ser. No. 08/391,663 entitled "PLASTIC ORTHODONTIC APPLIANCE HAVING A MECHANICAL BONDING BASE AND METHOD OF MAKING SAME", filed Feb. 21, 1995.

FIELD OF THE INVENTION

This invention relates to orthodontic brackets having rotation wings and, more particularly, to aesthetically pleasing plastic orthodontic brackets having rotation wings.

BACKGROUND OF THE INVENTION

In orthodontic treatment, tooth rotation, the movement of a tooth around its long axis, is considered to be one of the most difficult problems to solve. In order for an orthodontic archwire to exert an effective rotating force on a tooth, orthodontic brackets have evolved to include rotation wings. These rotation wings provide archwire contact points which are mesial and distal to the archwire slot and effectively increase the rotational force which can be exerted by an archwire on a tooth.

Rotation wing brackets developed to date include several all-metal brackets as well as a plastic bracket having metal rotation wings. The Lewis bracket and the Lang bracket are all-metal rotation wing brackets available in both weldable and bondable forms. Referring to FIG. 10, a bondable Lewis bracket is shown brazed to a foil mesh pad and available for bonding to a tooth. This particular bracket offers the orthodontist three potential archwire-contacting points for use in transferring a force from an archwire to a tooth. These three points include the two rotation wings as well as the center of the bottom wall of the archwire slot. However, because the Lewis bracket is brazed to a foil mesh pad, the braze rigidly bonds the rotation wings, thereby preventing adjustment of the rotation wings. Furthermore, the all-metal bracket does not offer the aesthetics of a bracket using non-metallic materials. The weldable version of the Lewis bracket does allow for some adjustment of the rotation wings because the bracket is welded to a band at a central point on the bracket and braze fill is not used. However, this option still offers limited aesthetic appeal.

The Lang bracket offers another rotation wing option in an all-metal weldable or bondable bracket. The rotation wings of this bracket are provided with no curvature and extend out from the archwire slot parallel with the bottom wall of the slot. In order for an orthodontist to adjust these rotation wings once the bracket is secured to a tooth and treatment is begun, the archwire must be removed from the bracket.

The Wick rotation wing bracket, a more recent development in an all-metal bondable bracket, offers several advantages over other all-metal rotation wing brackets. As can be seen in FIG. 11, although the body of the bracket is brazed to a foil mesh pad, the braze fill does not prevent adjustability of the rotation wings. Therefore, an orthodontist may achieve different degrees of rotational force without having to change the bracket on a particular tooth. Furthermore, because of the curvature of the rotation wings, an orthodontist may adjust the rotation wings once the bracket is on the tooth without having to remove the archwire. These advantages have made the Wick rotation wing bracket an attractive option when an all-metal bracket is desired.

Another option in the all-metal rotation wing bracket is the STYLE bracket sold by Ormco Corporation of Glendora, Calif. This single tie wing bracket offers the advantage of adjustable torque, The archwire slot and rotation wings are provided in a cylinder which may be rotated within the body housing to achieve the desired torque. Once the cylinder has been adjusted to the desired torque, it is brazed into place. The rotation wings of the STYLE bracket extend outwardly from the archwire slot along the same axis as the bottom wall of the slot. Therefore, if an orthodontist wishes to adjust either rotation wing once the bracket is positioned on a tooth, the orthodontic archwire must first be removed.

The use of rotation wings in an aesthetically pleasing plastic orthodontic bracket is taught by Reher et al. in U.S. Pat. No. 5,254,002. The '002 bracket is a translucent or transparent plastic bracket having a metal insert for reinforcing the archwire slot, thereby balancing the strength of an all-metal bracket with the aesthetically pleasing characteristics of a translucent or transparent plastic. The rotation wings on the '002 bracket extend straight out from the archwire slot parallel with the bottom wall of the slot. Therefore, when an archwire is placed in the archwire slot, an orthodontist is unable to adjust either rotation wing without first removing the orthodontic archwire. In addition, the metal insert of the '002 bracket has a mesial-distal wing span of about 0.14 in. from the outer end of one rotation wing to the outer end of the other rotation wing. This mesial-distal length is somewhat shorter than the mesial-distal length of the wings in several of the all-metal brackets. And although this reduced length places less stress on the metal insert within the plastic bracket, it also reduces the amount of rotational force which can be transferred from an orthodontic archwire to a tooth.

Therefore, it is desirable to have a single orthodontic bracket which provides both a highly aesthetically pleasing appearance and the ability to transfer significant rotational forces to a tooth. It also is desirable to have such an orthodontic bracket in which the rotation wings may be easily adjusted by an orthodontist without having to remove an archwire from the archwire slot.

SUMMARY OF THE INVENTION

This invention is directed to an orthodontic bracket having a plastic body including an archwire slot, a metal insert located in at least a portion of the archwire slot and having at least one rotation wing, and a protrusion extending into the archwire slot. More specifically, the plastic body includes an integrally connected tooth mountable base. The archwire slot of the plastic body is adapted to receive an orthodontic archwire, and includes a bottom wall and two opposing side walls extending from the bottom wall. The rotation wing of the metal insert is adapted to cooperate with an orthodontic archwire located in the archwire slot, in exerting a rotating force on a tooth via the base. In addition, the protrusion extending into the archwire slot has an upper end elevated above the bottom wall of the archwire slot. The upper end is adapted to contact the underside of an orthodontic archwire located in the archwire slot and to support at least a portion of the orthodontic archwire above the bottom wall of the archwire slot.

In a preferred form of the orthodontic bracket, the metal insert includes a bottom wall section and two opposing side walls. The protrusion is an integral part of the plastic body and extends into the archwire slot through a single opening formed in the bottom wall section and two opposing side walls. Furthermore, the protrusion preferably includes a flange which assists in securing the metal insert to the plastic body.

However, the protrusion and metal insert may be formed and positioned in any of a number of different ways, a few examples of which are discussed below. For example, the metal insert may include a bottom wall section, with the opening being formed in the bottom wall section, and the protrusion being an integral part of the plastic body and extending into the archwire slot through the opening, with the upper end of the protrusion being elevated above the opening. Alternatively, the metal insert may include two opposing side walls, with each of the opposing side walls having an opening. The protrusion then may be an integral part of the plastic body and extend into the archwire slot through the opening in each of the two opposing side walls. In another embodiment, the metal insert may include a bottom wall section, with the protrusion being an integral part of the plastic body and being disposed buccolabially relative to the bottom wall section. In another embodiment, the protrusion itself may be metal and be formed as an integral part of the metal insert.

With respect to the metal insert, the insert includes a central section, a first end section having an outer end and a second end section having an outer end, with the central section being disposed between the first and second end sections. At least one of the first and second end sections extends beyond the archwire slot and includes a rotation wing. And preferably, both first and second end sections extend beyond the archwire slot and include a rotation wing. In a preferred form of the invention, each of the rotation wings has an archwire-contacting section and an inner end integrally connected to the central section, with the archwire-contacting section having an occlusal-gingival width greater than the occlusal-gingival width of the archwire slot; and in a more preferred embodiment, this occlusal-gingival width tapers from the archwire contacting section toward the archwire slot. In a particularly preferred embodiment, the occlusal-gingival width of the archwire contacting section is about 0.04 in. and the metal insert has a mesial-distal length from the first end to the second end of about 0.2 in.

The tooth-mountable base of the orthodontic bracket preferably includes projecting structure extending outwardly from the base and adapted to mechanically bond the orthodontic bracket to a tooth surface with an adhesive. In a particularly preferred form of the invention, the projecting structure is a plurality of posts located on the base at the intersection points of an imaginary grid. Furthermore, the outer extremity or surface of the projecting structure is oriented so as to conform substantially to the curvature of a tooth.

Although various plastics and metals may be used, the plastic preferably is polycarbonate reinforced with glass fibers, with the glass fibers being present in an amount of from about 20% to about 40% by weight of the plastic. In addition, the metal insert preferably is made of 17-7 stainless steel, 300 Series stainless steel or MP35N alloy.

The orthodontic bracket of the present invention offers several benefits and advantages over other rotation wing brackets. For example, the bracket provides the ability to transfer enhanced rotational force in an attractive, aesthetically pleasing bracket without compromising the overall strength and integrity of the bracket. Also, because of the protrusion, an orthodontist is able to adjust the rotation wings without removing the archwire, regardless of the initial curvature of the wings. Furthermore, because brackets may be formed having protrusions with different heights, the slot depth or "in-out" dimension of the archwire slot may be specifically selected to achieve additional rotational control.

BRIEF DESCRIPTION OF THE DRAWINGS

FIG. 1 is a perspective view of a preferred embodiment of the orthodontic bracket;

FIG. 2 is a cross-sectional view of the embodiment of FIG. 1 taken along line 2—2;

FIG. 3 is a cross-sectional view of the embodiment of FIG. 1 taken along line 3—3;

FIG. 4 is a top view of the metal insert used in the embodiment of FIGS. 1–3;

DETAILED DESCRIPTION OF THE INVENTION

Figure 5:
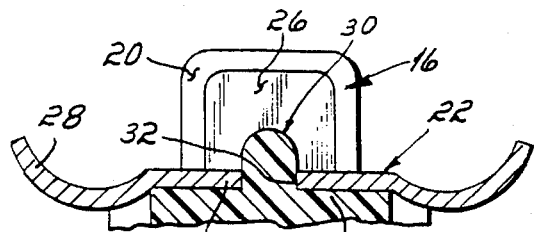
FIG. 5 is a partial cross-sectional view of another embodiment of the orthodontic bracket.

Referring to FIGS. 1–3, a preferred embodiment of the orthodontic bracket 10 includes a plastic body 12 having an integrally connected tooth-mountable base 14 and an archwire slot 16 for receiving an orthodontic archwire (not shown), with the slot 16 having a bottom wall 18 and two opposing side walls 20 extend from the bottom wall. The orthodontic bracket 10 also includes a metal insert 22 located in a portion of the archwire slot 16. The metal insert 22 shown has a bottom wall section 24 and two opposing side walls 26 extending from the bottom wall section 24. The metal insert 22 further includes a pair of rotation wings 28, with each rotation wing 28 extending outward from the archwire slot 16 and adapted to cooperate with an orthodontic archwire located in the archwire slot 16 in exerting a rotating force on a tooth via the bracket base 14. The orthodontic bracket 10 also includes a plastic protrusion 30 extending into the archwire slot 16 through an opening 32 in the bottom wall section 24 and opposing side walls 26 of the metal insert 22. The protrusion has an upper end 34 elevated above the bottom wall section 24 of the metal insert 22, with the upper end 34 being adapted to contact the underside of an orthodontic archwire located in the archwire slot 16 and to support at least a portion of the orthodontic archwire above the bottom wall section 24 of the metal insert 22. In addition, the protrusion 30 has dimensions which are slightly greater than the dimensions of the opening 32, thereby forming a flange 36 on the protrusion 30 which assists in securing the metal insert 22 to the plastic body 12.

The metal insert 22 used in the preferred embodiment shown in FIGS. 1–3 is shown in FIG. 4 in a partially formed condition. The insert 22 is shown in this generally flat position in order to better illustrate specific features of the insert 22. As shown, the metal insert 22 includes a central section 38, a first end section 40 and a second end section 42, with each end section having an outer end 44a, 44b. In this particular embodiment, each end section 40, 42 includes a rotation wing 28 having an archwire-contacting section 46 (see FIG. 2) and an inner end 48. The central section 38 includes a bottom wall section 24 and two opposing side walls 26 extending from the bottom wall section 24. Furthermore, a single opening 32 is formed in the bottom wall section 24 and the two opposing side walls 26. As seen in FIG. 4, this partially completed insert 22 is still attached to a runner 50 which is used in the forming process, allowing multiple inserts to be formed at the same time.

As best seen in FIGS. 1 and 4, the archwire-contacting section 46 of each rotation wing 28 has an occlusal-gingival width greater than the occlusal-gingival width of the rotation wing inner end 48. Furthermore, the occlusal-gingival width of the rotation wing 28 tapers gradually from the archwire-contacting section 46 to the inner end 48. This particular rotation wing design is preferred for several reasons. For example, because the archwire-contacting section 46 of each rotation wing 28 is wider than the archwire slot 16, the archwire-contacting section 46 has a greater surface area for meeting the archwire, thereby reducing any possibility that the archwire may become unintentionally disengaged from the rotation wing 28. Furthermore, because each rotation wing 28 tapers to a width generally approximating the width of the archwire slot 16, the wider archwire-contacting sections 46 may be provided while maintaining an overall appearance which is aesthetically pleasing. In a particularly preferred embodiment, each archwire-contacting section 46 has an occlusal-gingival width of about 0.04 in., with each rotation wing 28 tapering toward its inner end 48, each inner end 48 having an occlusal-gingival width of about 0.018 in. In addition, the particularly preferred metal insert 22 has a mesial-distal length of about 0.2 in, from the outer end 44a of the first end section 40 to the outer end 44b of the second end section 42. This mesial-distal length is preferred because each rotation wing 28 is long enough to transfer a substantial amount of force from an orthodontic archwire to a tooth, while at the same time, providing good rotation wing strength and an aesthetically pleasing size.

Referring to FIGS. 1 and 2, the rotation wings 28 of this particular embodiment are formed in a slightly concave, upswept position, with the archwire-contacting points 46 being positioned at the outer ends 44a, 44b of the rotation wings 28. However, each rotation wing may be provided with any particular angle or curvature, or with no angle at all, as is understood by one of ordinary skill in the art. Furthermore, an orthodontist may adjust each rotation wing as desired in order to achieve the rotation needed for a particular patient. For example, as shown by the arrows and phantom rotation wing lines in FIG. 2, either rotation wing 28 may be adjusted as desired.

Referring to FIGS. 1–3, the protrusion 30 of the orthodontic bracket 10 has a particular height, length, width and contour. However, any of these dimensions may be adjusted as desired, for example, simply by using a thermoplastic injection mold having a different protrusion forming cavity. The only requirement is that the upper end 34 of the protrusion 30 extend above the bottom wall 18 of the archwire slot 16, which typically is formed by the bottom wall section 24 of the metal insert 22. For example, the buccolabial height of the protrusion may be varied to create brackets having different archwire slot depths or "in-out" dimensions. These different slot depths enable rotational forces to be selected not only by the angles of the adjustable rotation wings, but by the particular height of the protrusion.

Referring to FIGS. 1 and 2, the tooth-mountable base 14 of the preferred orthodontic bracket 10 includes a plurality of posts 52 located on the base 14 at the intersection points of an imaginary grid and extending outwardly from the base, as described in copending application Ser. No. 08/391,663 which is commonly assigned and incorporated herein in its entirety by reference. As shown in FIGS. 1 and 2, each post 52 includes an inner extremity 54 integrally connected to the base 14, an outer extremity 56 and an intermediate section 58 between the inner and outer extremity 54, 56. Furthermore, the cross-sectional area of the outer extremity 56 is greater than the cross-sectional area of the intermediate section 58, thereby forming an undercut 60 in each post 52 to facilitate mechanical bonding of the orthodontic bracket 10 to a tooth surface using an adhesive. These posts 52 preferably are formed as described in application Ser. No. 08/391,663.

Although the embodiment shown in FIGS. 1–3 includes a single tie wing 62, it is to be understood that the orthodontic bracket may be formed to include any of a number of additional or alternative shapes and features. For example, the orthodontic bracket may be equipped with double tie wings or with no tie wings at all. Additionally, the bracket may be formed with other features such as, for example, hooks or other features as are known in the art.

Although any suitable plastic may be used for the orthodontic bracket, the plastic preferably is polycarbonate reinforced with glass fibers, with the glass fibers representing from about 20% to about 40% by weight of the plastic. This particularly preferred plastic composition and method of forming a plastic bracket are taught in Reher et al. U.S. Pat. No. 5,254,002 assigned to Ormco Corporation, which is incorporated herein in its entirety by reference. With respect to the metal insert, any suitable metal may be used. However, it is preferred to use 17-7 stainless steel, 300 Series stainless steel or MP35N alloy. Suitable 17-7 stainless steel is available from Ulbrich of California, Inc., of Fresno, Calif. If 17-7 annealed stainless steel is used, the stainless steel typically will require some amount of heat treatment as is understood in the art, in order to add temper to the metal. However, if Condition C 17-7 stainless steel is used, little or no heat treatment is required. If 300 Series stainless steel is used, it preferably is hardened by cold working to a tensile strength of greater than about 100,000 psi. Alternatively, a nickel-cobalt based alloy sold by Climax Specialty Metals, of Cleveland, Ohio under the trade name CLIMAX MP35N ALLOY may be used. Because this particular alloy has a dual-grain boundary and a higher temper, it is possible to avoid the extra heat treatment step required when using some other metals.

The orthodontic bracket preferably is formed by first forming the metal insert and then injection molding the plastic bracket around the insert. If desired, several metal inserts may be formed simultaneously in a progressive die with each of the inserts being connected by a common runner. For example, in blanking out the metal sheeting, one die station may cut the top half of each insert and a subsequent station may cut the bottom half of each insert. In a subsequent station, an oval punch cuts a pierced hole or opening in each insert. In subsequent steps, the progressive die partially uprights the side walls, and a sizing tool is used to reiron or rewipe the inserts to their finished dimensions. At this point, any outer rail metal material is cut from the inserts which are still connected by a central runner. If desired, the central runner may be cut into sections, resulting in pairs of inserts connected by a central runner. At this point, if heat treatment is required, the inserts may be placed in a heating boat which is put into a furnace for heat treatment. If Condition C 17-7 stainless steel is used, the inserts preferably are heat treated at about 900° C. for approximately 60 minutes.

At this point, the insert pairs are placed in a thermal plastic injection molding machine and plastic is injected into the mold to form the orthodontic bracket. The posts of the tooth-mountable base are formed as taught in copending application Ser. No. 08/391,663 in a multistage process. As taught in that application, undeformed posts are formed in the initial plastic injection molding step, and the outer ends of the posts are deformed in a subsequent step to provide the undercuts useful in mechanically bonding the bracket to a tooth surface. Once the posts have been deformed, the runner and any excess steel is removed from the inserts. At this point, if it is desired to place some curvature in the rotation wings, the rotation wings are bent manually using a mandrel.

In use, the orthodontic bracket is adhered to a tooth requiring some degree of rotation. Based upon the degree of rotation required, the orthodontist may adjust the shape of each rotation wing as desired. For example, if an orthodontist desires the archwire to contact the projection and both rotation wings, the rotation wings may be adjusted to achieve such a three-point contact. On the other hand, if a particular rotation requires only a two-point contact, the orthodontist may adjust the wings to achieve such contact, with the two points being either the two rotation wings, or a rotation wing and the protrusion.

Although the invention has been described above in connection with a particularly preferred embodiment, the inventive orthodontic bracket may have component parts with different shapes and may be formed in various ways, as long as the bracket includes a plastic body, a metal insert secured to the plastic body and having a rotation wing, and a protrusion extending into the archwire slot. Just a few of the many alternative embodiments are shown in FIGS. 5–9. In the embodiment shown in FIG. 5, the metal insert 22 includes an opening 32 which does not extend to the side walls 26 of the insert 22, but which is confined to the bottom wall section 24. Furthermore, the plastic protrusion 30 extending into the archwire slot 16 does not include a flange, and the insert 22 is secured to the plastic body 12 by the insert side walls 26 which form a portion of the side walls 20 of the archwire slot 16. If, on the other hand, the protrusion were formed to include a flange, then the metal insert side walls would not be needed.

Figure 6:
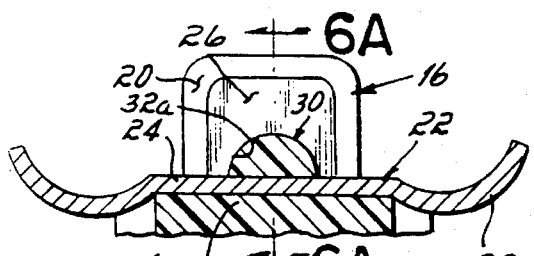
FIG. 6 is a partial cross-sectional view of an alternative embodiment of the orthodontic bracket.
Figure 6A:
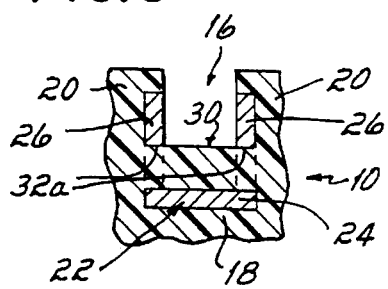
FIG. 6A is a partial cross-sectional view of the embodiment of FIG. 6 taken along line 6A—6A.
Figure 6B:
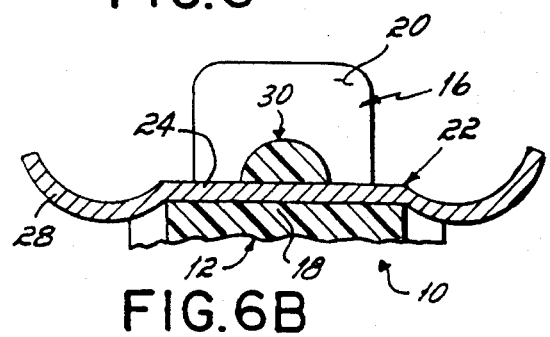
FIG. 6B is a partial cross-sectional view of a further embodiment of the orthodontic bracket.

In the embodiment shown in FIGS. 6 and 6A, the metal insert 22 does not include an opening in the bottom wall section 24. Instead, each of the opposing side wall sections 26 of the insert 22 includes a hemispherical opening 16 allowing for the passage of plastic through the openings 16 and into the archwire slot 16 during thermoplastic injection molding. In this particular embodiment, the resulting protrusion 30 assists in securing the metal insert 22 to the plastic body in conjunction with the insert side walls 26, despite the fact that the insert 22 has no opening in the bottom wall section 24. As shown in FIG. 6B, a metal insert 22 having no side walls and no opening whatsoever may be secured to the plastic body 12 simply by forming a plastic protrusion 30 buccolabially above the metal insert bottom wall section 24 and integrally connected with each of the opposing side walls 20 of the archwire slot 16.

Figure 7:
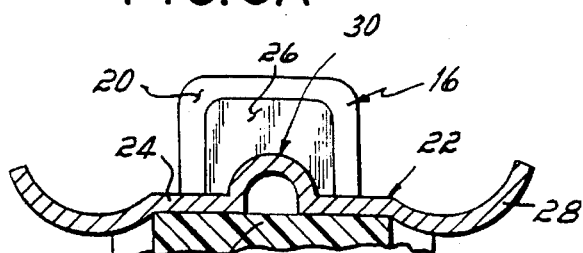
FIG. 7 is a partial cross-sectional view of yet another embodiment of the orthodontic bracket.
Figure 8:
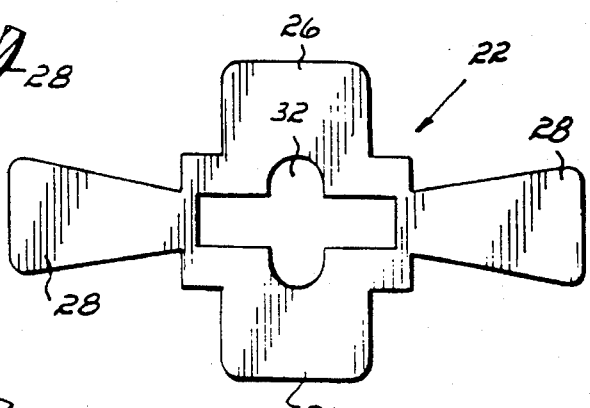
FIG. 8 is a top view of an alternative metal insert for use in the orthodontic bracket.
Figure 9:
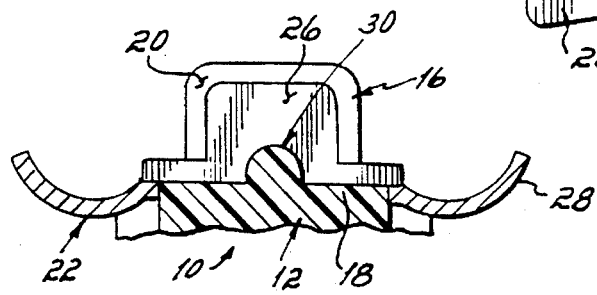
FIG. 9 is a partial cross-sectional view of an alternative embodiment of the orthodontic bracket incorporating the metal insert of FIG. 8.
Figure 10:
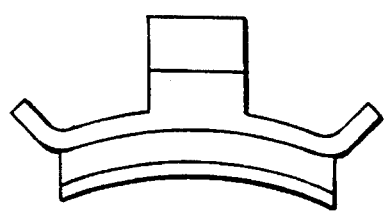
FIG. 10 is a side view of a prior art orthodontic bracket.
Figure 11:
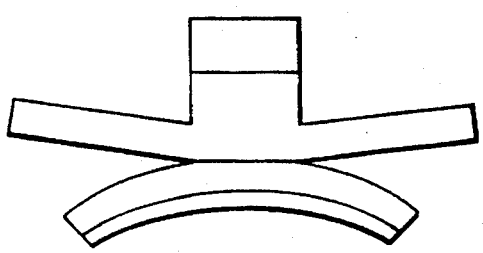
FIG. 11 is a side view of another prior art orthodontic bracket.

In the embodiment shown in FIG. 7, the protrusion 30 is formed, not of plastic, but of metal, and is integral with the bottom wall section 24 of the metal insert 22. The embodiment of FIG. 9 incorporates the metal insert 22 shown in FIG. 8. In this particular embodiment, the opening 32 replaces the preferred bottom wall section 24 and a portion of each of the insert side walls 26; and therefore no metal insert material will cover the plastic bottom wall 18 of the archwire slot 16.

Although a few particular embodiments of the present invention have been discussed above, it will readily understood by those of ordinary skill in the art that several other variations and modifications may be made, and accordingly, the scope of the invention is determined by the following claims.

What is claimed is:

1. An orthodontic bracket, comprising:
   a plastic body including an integrally connected tooth-mountable base, said body including an archwire slot for receiving an orthodontic archwire, said slot having a bottom wall and two opposing sidewalls extending therefrom;
   a metal insert located in at least a portion of said archwire slot and having at least one rotation wing, said rotation wing adapted to cooperate with an orthodontic archwire located in said archwire slot in exerting a rotating force on a tooth via said base; and
   a protrusion extending into said archwire slot, said protrusion having an upper end elevated above said bottom wall of said archwire slot, said upper end adapted to contact the underside of an orthodontic archwire located in said archwire slot and support at least a portion of the orthodontic archwire above said bottom wall of said archwire slot.

2. The orthodontic bracket of claim 1 wherein said protrusion extends into said archwire slot through an opening in said metal insert.

3. The orthodontic bracket of claim 2 wherein said metal insert includes a bottom wall section, said opening being formed in said bottom wall section, said protrusion being an integral part of said plastic body and extending into said archwire slot through said opening, said upper end of said protrusion being elevated above said opening.

4. The orthodontic bracket of claim 2 wherein said metal insert includes two opposing sidewalls, each of said two opposing sidewalls having an opening, said protrusion being an integral part of said plastic body and extending into said archwire slot through said opening in each of said two opposing sidewalls.

5. The orthodontic bracket of claim 2 wherein said metal insert includes a bottom wall section and two opposing sidewalls, said protrusion being an integral part of said plastic body and extending into said archwire slot through an opening formed in said bottom wall section and two opposing sidewalls.

6. The orthodontic bracket of claim 2 wherein said protrusion includes a flange, said flange assisting in securing said metal insert to said plastic body.

7. The orthodontic bracket of claim 5 wherein said protrusion includes a flange, said flange assisting in securing said metal insert to said plastic body.

8. The orthodontic bracket of claim 1 wherein said metal insert includes a bottom wall section, said protrusion being an integral part of said plastic body and being disposed buccolabially relative to said bottom wall section, thereby assisting in maintaining said metal insert bottom wall section in said archwire slot.

9. The orthodontic bracket of claim 1 wherein said protrusion is metal and is an integral part of said metal insert.

10. The orthodontic bracket of claim 1 wherein said metal insert includes a central section, a first end section having an outer end and a second end section having an outer end, said central section disposed between said first and second end sections, at least one of said first and second end sections extending beyond said archwire slot and including said rotation wing.

11. The orthodontic bracket of claim 10 wherein said rotation wing has an archwire-contacting section and an inner end integrally connected to said central section, said archwire-contacting section having an occlusal-gingival width greater than the occlusal-gingival width of said archwire slot.

12. The orthodontic bracket of claim 11 wherein the occlusal-gingival width of said rotation wing tapers from said archwire-contacting section to said archwire slot.

13. The orthodontic bracket of claim 11 wherein said occlusal-gingival width of said archwire-contacting section is about 0.04 in.

14. The orthodontic bracket of claim 10 wherein the other one of said first and second end sections extends beyond said archwire slot and includes a second rotation wing.

15. The orthodontic bracket of claim 14 wherein said metal insert has a mesial-distal length from said outer end of said first end section to said outer end of said second section end section of about 0.2 in.

16. The orthodontic bracket of claim 1 wherein said base includes projecting structure extending outwardly from said base, said projecting structure having an inner extremity integrally connected to said base, an outer extremity and an intermediate section between said inner and outer extremities, the cross-sectional area of said outer extremity being greater than the cross-sectional area of the intermediate section, thereby forming undercuts in said projecting structure to facilitate mechanically bonding said orthodontic bracket to a tooth surface with an adhesive.

17. The orthodontic bracket of claim 16 wherein said outer extremity of said projecting structure is oriented so as to conform substantially to the curvature of a tooth.

18. The orthodontic bracket of claim 17 wherein said projecting structure is a plurality of posts.

19. The orthodontic bracket of claim 18 wherein said posts are located on said base at the intersection points of an imaginary grid.

20. The orthodontic bracket of claim 1 wherein said plastic is polycarbonate reinforced with glass fibers.

21. The orthodontic bracket of claim 20 wherein said glass fibers are present in an amount of from about 20% to about 40% by weight of said plastic.

22. The orthodontic bracket of claim 1 wherein said metal insert is made of a metal selected from the group consisting of 17-7 stainless steel, 300 Series stainless steel and MP35N Alloy.

23. An orthodontic appliance, comprising:

an orthodontic bracket having a plastic body including an integrally connected tooth-mountable base, said base adhered to a tooth surface with an adhesive, said body including an archwire slot for receiving an orthodontic archwire, said slot having a bottom wall and two opposing sidewalls extending therefrom;

a metal insert located in at least a portion of said archwire slot and having at least one rotation wing, said rotation wing adapted to cooperate with an orthodontic archwire located in said archwire slot in exerting a rotating force on a tooth via said base;

a protrusion extending into said archwire slot, said protrusion having an upper end elevated above said bottom wall of said archwire slot, said upper end adapted to contact the underside of an orthodontic archwire located in said archwire slot and support at least a portion of the orthodontic archwire above said bottom wall of said archwire slot; and an archwire disposed within said archwire slot for transferring a force to the tooth.

* * * * *